United States Patent
Bybee et al.

(10) Patent No.: US 6,177,050 B1
(45) Date of Patent: Jan. 23, 2001

(54) CONTAINER POSITIONING DEVICE

(75) Inventors: Thomas L. Bybee; Inna M. Zevakina, both of Omaha, NE (US)

(73) Assignee: LAB-Interlink, Inc., Omaha, NE (US)

( * ) Notice: Under 35 U.S.C. 154(b), the term of this patent shall be extended for 0 days.

(21) Appl. No.: 09/193,999

(22) Filed: Nov. 18, 1998

(51) Int. Cl.[7] .................................................. G01N 31/00
(52) U.S. Cl. ................... 422/65; 422/63; 422/67; 422/99; 422/104; 422/107; 422/108; 436/47; 436/48
(58) Field of Search ................................. 422/63, 65, 66, 422/67, 99, 100, 104, 107; 436/47, 48

(56) References Cited

U.S. PATENT DOCUMENTS

| | | | | |
|---|---|---|---|---|
| 4,391,774 | * | 7/1983 | Dupain | 422/63 |
| 4,835,707 | * | 5/1989 | Amano et al. | 364/497 |
| 4,951,513 | * | 8/1990 | Koike | 73/864.25 |
| 5,080,864 | * | 1/1992 | Shaw | 422/62 |
| 5,158,985 | * | 10/1992 | Ashihara et al. | 436/526 |
| 5,221,519 | * | 6/1993 | Wuerschum | 422/65 |
| 5,417,922 | * | 5/1995 | Markin et al. | 422/65 |
| 5,427,743 | * | 6/1995 | Markin | 422/104 |
| 5,525,298 | * | 6/1996 | Anami | 422/63 |
| 5,589,137 | * | 12/1996 | Markin et al. | 422/104 |
| 5,665,309 | * | 9/1997 | Champseix et al. | 422/63 |
| 5,948,360 | * | 9/1999 | Rao et al. | 422/65 |

* cited by examiner

Primary Examiner—Jill Warden
Assistant Examiner—Patricia Kathryn Bex
(74) Attorney, Agent, or Firm—Koley Jessen P.C.; Mark D. Frederiksen

(57) ABSTRACT

A container positioning device includes a stop mechanism for stopping a carrier moving along a conveyor, the carrier supporting a container thereon. A pair of arms are pivotally mounted to move between an open position permitting the container to pass along the conveyor track, and a centering position with forward ends in contact with the container and positioning the container in a centering location. A forward end of the downstream arm is operable to move upstream and contact the container to move the container upstream to the centering location, where the second arm will contact the container to retain it in place.

12 Claims, 4 Drawing Sheets

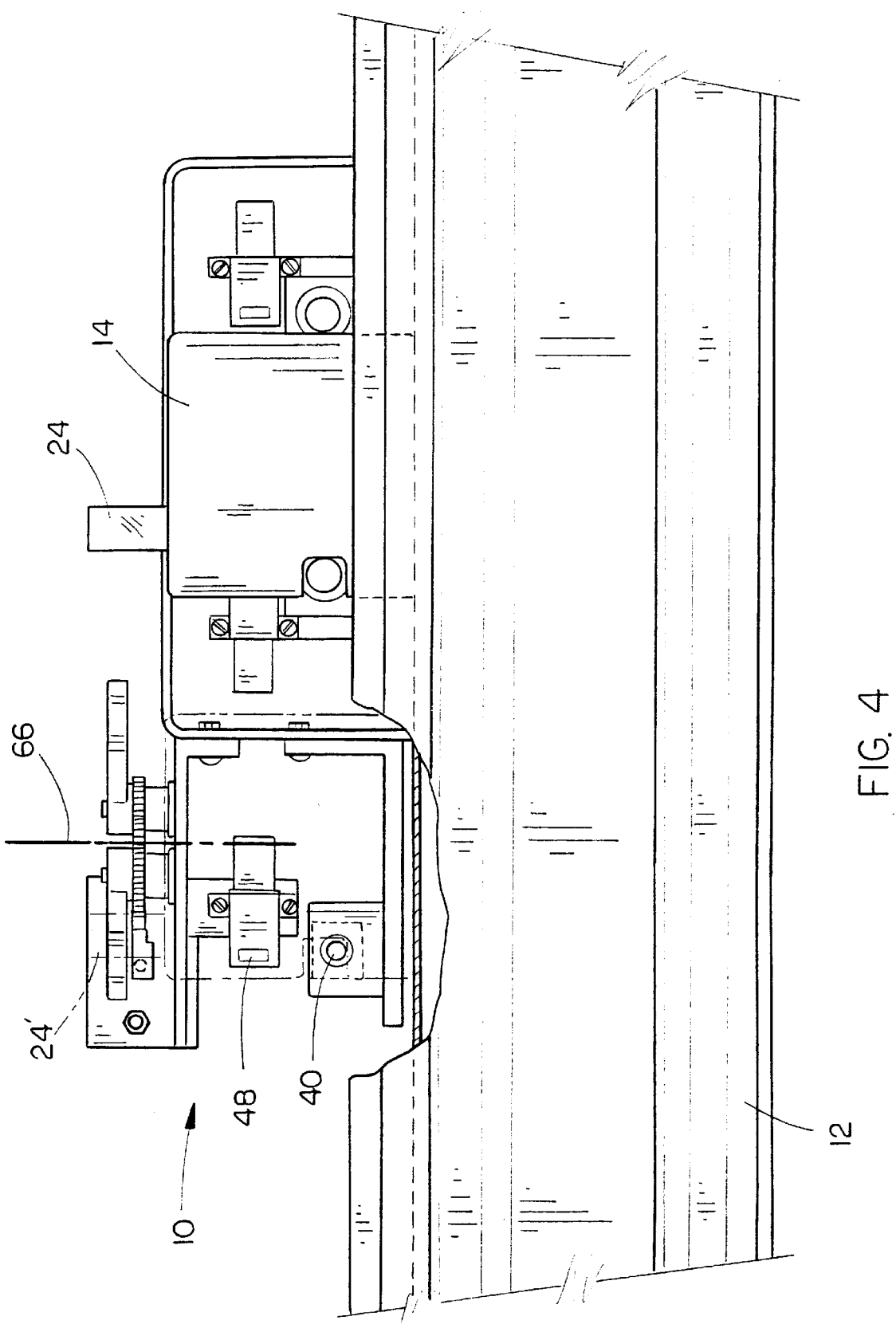

CONTAINER POSITIONING DEVICE

TECHNICAL FIELD

The present invention relates generally to laboratory conveyor and testing systems, and more particularly to an improved apparatus for positioning a specimen container in a predetermine location for retrieval by a robotic arm of an automated laboratory system.

BACKGROUND OF THE INVENTION

Automated laboratory systems utilize standardized carrier units which travel about conveyors or are otherwise transported throughout a laboratory, to convey individual specimen containers to various testing apparatus. Examples of such specimen carriers may be found in U.S. Pat. No. 5,589,137 to Markin et al., U.S. Pat. No. 5,417,922 to Markin et al., and U.S. Pat. No. 5,427,743 to Markin. Each of the specimen carriers noted above includes a plurality of openings having various depths and sizes for the receipt of a variety of sizes of specimen containers, including test tubes, vials and the like.

Robotic equipment utilized to retrieve an individual specimen container from a specimen carrier unit is programmed to move a pair of grasping jaws to a predetermine location, clamp the jaws together about the specimen container located at the location, and then raising and transporting the specimen container to the desired location. However, the use of a specimen carrier which provides a plurality of locations in which the specimen container may be located and/or a plurality of sizes of specimen container, causes a problem for such robotic equipment. It is difficult and complicated to program a piece of robotic equipment to detect the specific location of a specimen container within a specimen carrier, center the grasping arms at the sensed location of the container, and then grasp and remove the container. In order to assure that the robotic arm will securely grasp and remove the specimen container, the container must be precisely positioned at a single predetermined location programmed into the robotic arm.

This also can be a problem with a specimen carrier having only a single opening for a specimen container. If the carrier is not stopped and positioned precisely, the robotic arm may not properly grasp and remove a specimen container from the carrier, or may completely miss the container.

SUMMARY OF THE INVENTION

It is therefore a general object of the present invention to provide an improved apparatus for positioning a specimen container at a predetermined location for retrieval by a robotic arm of an automated system.

Still another object is to provide a container positioning device which will precisely locate a container supported in one of a plurality of possible positions within a carrier for retrieval by a robotic arm.

A further object of the present invention is to provide a specimen container positioning device which is simple to use, and economical to manufacture.

These and other objects of the present invention will be apparent to those skilled in the art.

The container positioning device of the present invention includes a stop mechanism for stopping a carrier moving along a conveyor, the carrier supporting a container thereon. A pair of arms are pivotally mounted to move between an open position permitting the carrier to pass along the conveyor track, and a centering position with forward ends in contact with the container and positioning the container in a centering location. A forward end of a downstream arm is operable to move upstream and contact the container to move the container upstream to the centering location, where the second arm will contact the container to retain it in place.

BRIEF DESCRIPTION OF THE DRAWINGS

FIG. 4 is a front elevational view of the positioning device of the present invention.

DESCRIPTION OF THE PREFERRED EMBODIMENT

Figure 1:
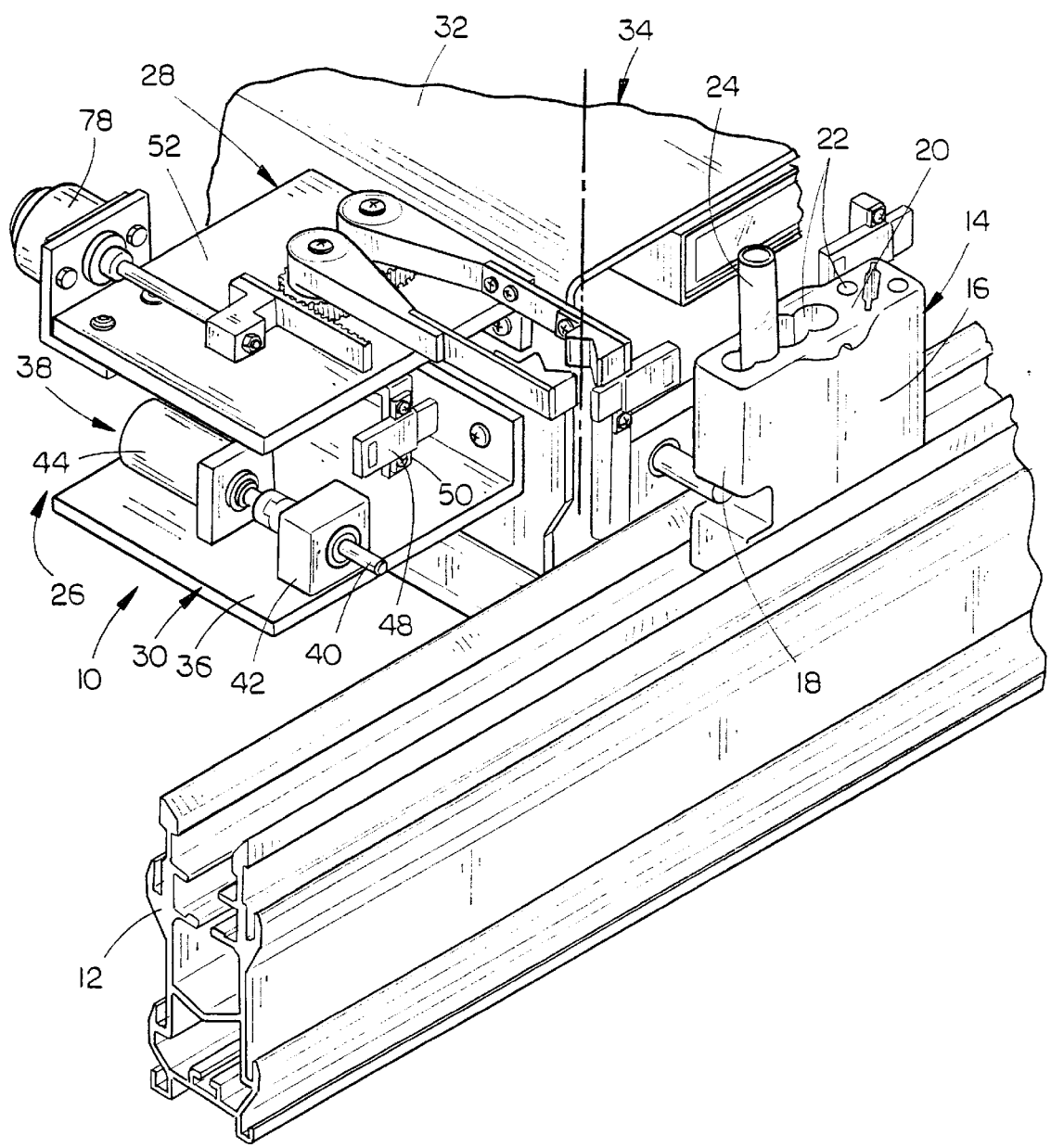
FIG. 1 is a perspective view of the positioning device of the present invention installed on a laboratory conveyor system.

Referring now to the drawings, in which similar or corresponding parts are identified with the same reference numeral and more particularly to FIG. 1, the specimen container positioning device of the present invention is designated generally at 10 and is shown mounted adjacent a conveyor track 12 of an automated laboratory system. The conveyor track transporting a plurality of specimen carriers 14 throughout a laboratory or the like.

One embodiment of a specimen carrier 14 is disclosed in detail throughout these drawings, but it should be understood that many other sizes and shapes of carriers for specimen containers could be utilized with the present invention Specimen carrier 14 includes a generally rectangular body 16 with a forward wall 18 and a top surface 20. A plurality of openings 22 are formed in top surface 20 down into the interior of body 16, for supporting a specimen container 24 in an upright orientation with an upper end projecting above the top surface of carrier 14. As shown in FIG. 1, openings 22 may be of various diameters, may be separated or overlapping, and may be of various depths, to provide for specimen containers 24 of a variety of shapes and sizes.

Figure 2:
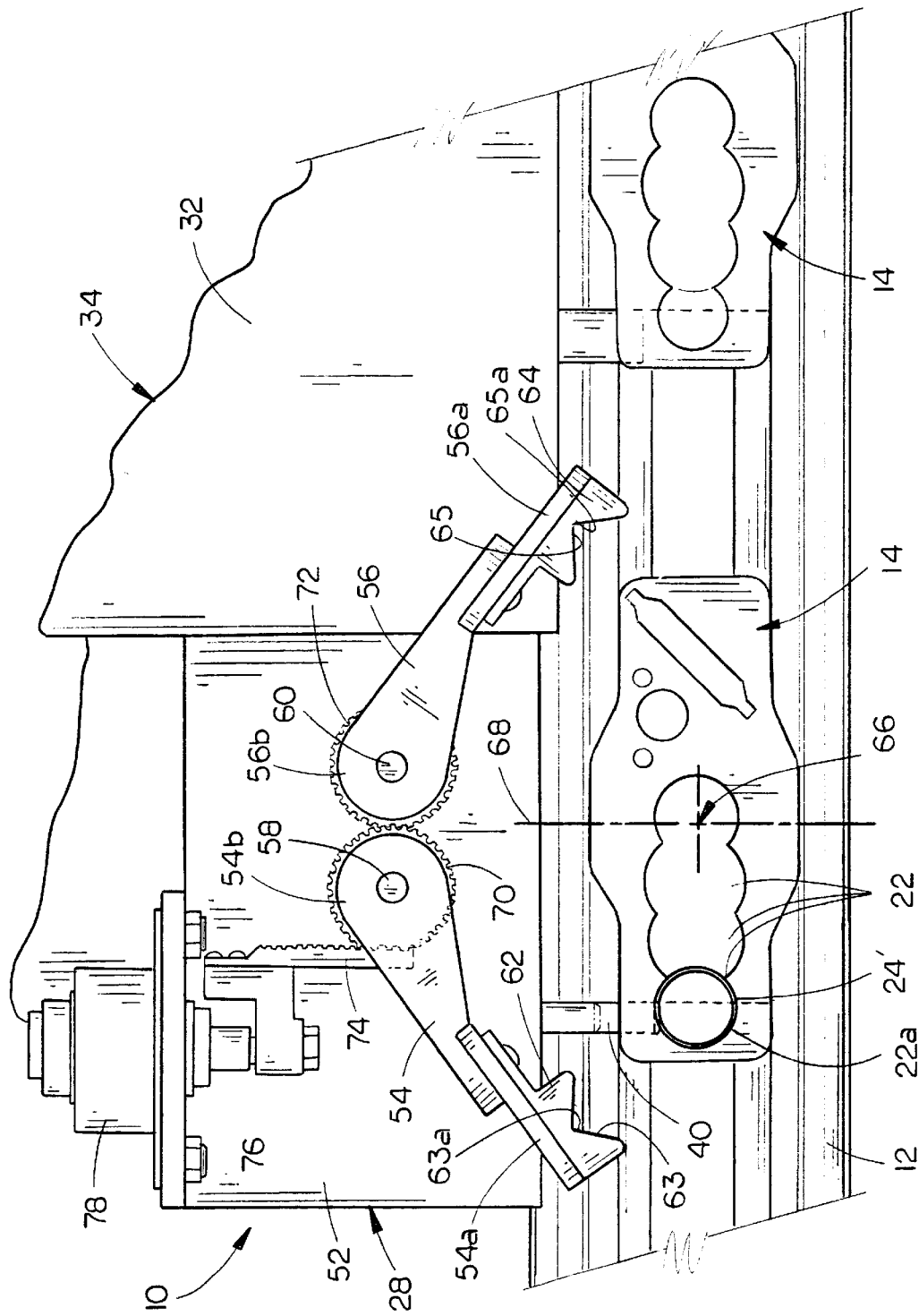
FIG. 2 is a top plan view of the positioning device in a first position.

Positioning device 10 includes a support frame 26 comprised of an upper bracket 28 and a lower bracket 30 both of which are mounted to a mounting frame 32. Mounting frame 32 is preferably part of an automated queue 34 utilized to selectively stop and stack carriers 14 for detection and tracking by the automated conveyor system. Lower bracket 30 includes a horizontally projecting base plate 36 which supports an operable queuing apparatus 38, utilized to selectively stop the movement of a specimen carrier 14 along conveyor track 12. Queuing apparatus 38 includes an extensible and retractable pin 40 mounted in a bearing block 42 and connected at a rearward end to a cylinder 44 for selectively extending and retracting pin 40. As shown in FIG. 2, pin 40 may be extended transversely over the top of track 12 to project within the path of movement of specimen carriers 14 so as to selectively stop and queue the specimen carrier for centering by positioning device 10. Cylinder 44 is electronically connected to a central processing unit of automated queue 34 (shown in FIG. 1) for selective operation.

A sensor 48 is supported on a bracket 50 which depends from the bottom of the base plate 52 of upper bracket 28, and is arranged to detect the presence or absence of a specimen carrier 14 on track 12 in front of centering device 10. Sensor 48 is also electronically connected to the central processing unit (CPU) of queue 34.

Figure 3:
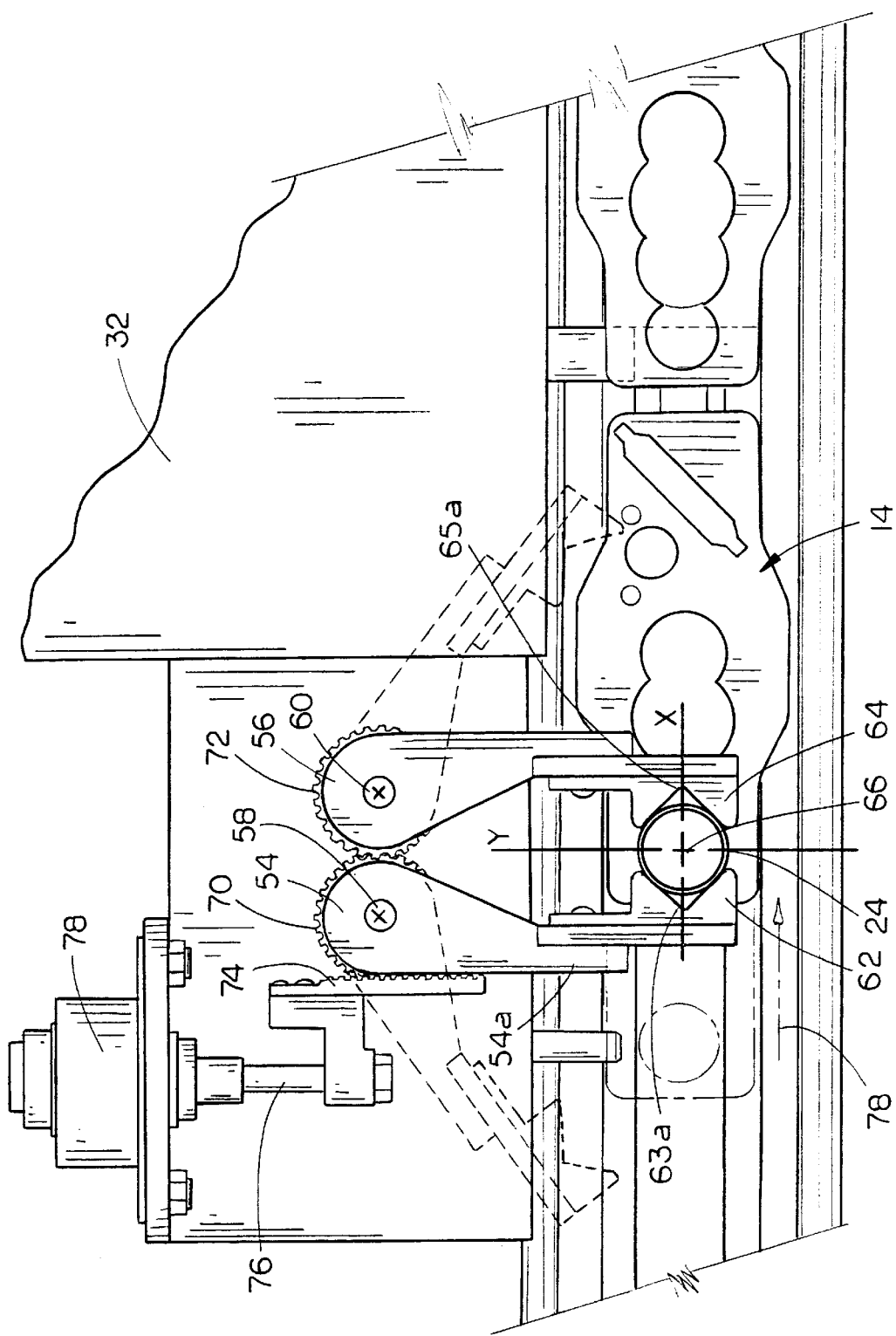
FIG. 3 is a top plan view of the positioning device in a second position centering a specimen container.

Referring now to FIGS. 2 and 3, a pair of positioning arms 54 and 56 are pivotally mounted at rearward ends of pivot pins 58 and 60 respectively, for pivotal movement within a horizontal plane between an open position, shown in FIG. 2, and a closed/centering position shown in FIG. 3. The forward ends 54a and 56a of arms 54 and 56 have pads 62 and 64 mounted thereon with a contact surface 63 and 65 respectively. Contact surfaces 63 and 65 are preferably formed in a "V-shape" when viewed form above, with a pair of surfaces sloped rearwardly and inwardly towards the arms 54 and 56. The valleys 63a and 65a of each contact surface 63 and 65, are oriented vertically and aligned along the longitudinal axis X of the conveyor track 12, as shown in FIG. 3. In this way, specimen containers 24 of various sizes and diameters will be centered along the X axis upon closing of arms 54 and 56.

Arms 54 and 56 must be pivotable outwardly to an open position with the forward ends 54a and 56a thereof clear of specimen containers 24 in specimen carriers 14 on track 12, to permit movement of the specimen containers 24 past arms 54 and 56. Similarly, pivot arms 54 and 56 have a length, and are positioned such that contact surface 63 of pad 62 will reach and contact a specimen container 24 located in the forward most opening 22a in specimen container 14 (shown in FIGS. 2).

Positioning device 10 is mounted on mounting frame 32 such that arms 54 and 56 will position a specimen container 24 at a predetermined centering location identified generally at 66 in FIG. 2. A transverse Y axis, perpendicular to the longitudinal X axis of track 12, passing through centering location 66, will pass midway between arms 54 and 56, to accurately position the specimen container at the predetermined centering location 66, for access and/or retrieval by a robotic arm.

The rearward ends 54b and 56b of arms 54 and 56 have pinions 70 and 72 respectively rotatably mounted on pivot pins 58 and 60, with teeth that intermesh. thus, pivotal movement of arm 54 will rotate pinion 70, which in turn has teeth which intermesh with pinion 72 so as to pivot arm 56 in the opposite direction. Arms 54 and 56 will pivot simultaneously in opposing directions on pivot pins 58 and 60. A rack 74 is mounted to a plunger 76 on a cylinder 78, for selective movement between a first position, shown in FIG. 2, and a second position shown in FIG. 3. Rack 74 is moved along its longitudinal axis between the first and second positions, and has teeth which mesh with the teeth of pinion 70. Rack 74 is operable tangent to pinion 70, in a conventional fashion, such that movement of rack 74 between the first and second positions will cause the rotation of pinion 70 between the open and centered positions respectively.

Plunger 76 is selectively extended and retracted by cylinder 78, which is electronically connected to the CPU of automated queue 34 (shown in FIG. 1) for selective operation. Although the preferred embodiment of the invention utilizes intermeshing pinions 70 and 72 and an operable rack 74 to selectively pivot arms 54 and 56, it should be understood that there are a wide variety of equivalent apparatus which may be utilized to obtain the desired pivotal movement of these arms. In addition, it is possible to obtain the centering of specimen container 24 using only the downstream positioning arm 54, although such an arrangement is not preferred.

In operation, the CPU of automated queue 34 will be programmed with information relative to particular specimen carriers 14 which are required to be stopped such that a specimen container 24 may be retrieved or the specimen therein sampled, as shown in FIGS. 1 and 4. The CPU of queue 34 will cause pin 40 to be extended over track 12, and thereby stop a carrier 14 in front of positioning device 10. As shown in broken lines in FIG. 4, specimen container 24' is positioned downstream of centering location 66, when pin 40 stops carrier 14. The position of specimen container 24' is shown in solid lines in FIG. 2, while arms 54 and 56 are in the open position.

Once sensor 48 (shown in FIGS. 1 and 4) detects the presence of a carrier 14, cylinder 78 is actuated to move rack 74 from the first position shown in FIG. 2 to the second position shown in FIG. 3. This movement of rack 74 will rotate pinion 70 and thereby rotate pinion 72, to pivot the downstream arm 54 in an upstream direction, and pivot the upstream arm 56 in the downstream direction, to the centering location 66 shown in FIG. 3. It can be seen that movement of downstream arm 54 in the upstream direction will cause the forward end 54a and pad 62 of downstream arm 54 to contact container 24 and move it (along with carrier 14) upstream to the centering location 66, as shown by arrow 78 in FIG. 3. Because arms 54 and 56 are moved simultaneously, pad 64 on upstream arm 56 will contact specimen container 24 when it reaches centering location 66.

As noted above, the centering function could be accomplished by the single downstream arm 54 of the present invention. However, it would be necessary to stop the pivotal movement of arm 54 at the appropriate position, such that specimen container 24 is located at centering position 66. The use of a second arm 56 accomplishes this function without requiring detectors or other sensors for determining the location of the specimen container in the specimen carrier.

Whereas the invention has been shown and described in connection with the preferred embodiment thereof, many modifications, substitutions and additions may be made which are within the intended broad scope of the appended claims.

We claim:

1. An apparatus for positioning a container carried in a carrier at a predetermined centering location along a conveyor track, comprising:

an operable stop mechanism, operable to stop a carrier moving along the conveyor track;

a first positioning arm operably mounted on a frame adjacent the track, operable between an open position located downstream of the centering location and clear of the track to permit carriers to move past the arm, and a centering position upstream of the open position and extending across a portion of the track to contact and move a container supported in a carrier stopped by the stop mechanism to the centering location;

means for selectively moving the first arm between the open and centering positions;

said first arm being pivotally mounted at a rearward end for movement of a forward end thereof through a generally horizontal plane, the forward end of the first arm contacting the container when the first arm is moved to the centering position;

a second positioning arm operably mounted on said frame and operable between an open position located upstream of the centering location and clear of the track to permit containers to move past the second arm, and a centering position downstream of the open position and in contact with the container in the carrier moved to the centering location; and means for selectively moving the second arm between the open and centering positions.

2. The apparatus of claim 1, wherein said first and second arms are operably connected for simultaneous movement between the open and centering position.

3. The apparatus of claim 2, wherein said second arm is pivotally mounted at a rearward end of movement of a forward end thereof through a generally horizontal plane, the forward end of the second arm contacting the container when the second arm is moved to the centering position.

4. The apparatus of claim 3, further comprising a sensor mounted adjacent the track for sensing the presence of a carrier stopped at said stop mechanism.

5. The apparatus of claim 4, further comprising a central processing unit electronically connected to the stop mechanism, the sensor, and the means for moving said first and second arms, said central processing unit operable to selectively actuate the stop mechanism to stop a carrier and to operate the means for selectively moving the first and second arms upon detection of a carrier by the sensor.

6. The apparatus of claim 5, wherein the forward ends of said first and second arms each have a contact surface for contacting the container.

7. The apparatus of claim 6 wherein each said contact surface has a shape which will center the container along a longitudinal axis of the conveyor track when the arms are moved to the centering position.

8. An apparatus for positioning a container carried in a carrier at a predetermined centering location along a conveyor track, comprising:

an operable stop mechanism, operable to stop a carrier moving along the conveyor track;

a first positioning arm operably mounted on a frame adjacent the track, operable between an open position located downstream of the centering location and clear of the track to permit carriers to move past the arm, and a centering position upstream of the open position and extending across a portion of the track to contact and move a container supported in a carrier stopped by the stop mechanism to the centering location;

means for selectively moving the first arm between the open and centering positions, a second positioning arm operably mounted on said frame and operable between an open position located upstream of the centering location and clear of the track to permit containers to move past the second arm, and a centering position downstream of the open position and in contact with the container in a carrier moved to the center location; and means for selectively moving the second arm between the open and centering positions.

9. The apparatus of claim 8, wherein said first and second arms are operably connected for simultaneous movement between the open and centering positions.

10. The apparatus of claim 9, wherein said second arm is pivotally mounted at a rearward end for movement of a forward end thereof through a generally horizontal plane, the forward end of the second arm contacting the container in the centering positions.

11. The apparatus of claim 8, further comprising a sensor mounted adjacent the track for sensing the present of a carrier stopped at said stop mechanism.

12. The apparatus of claim 8, further comprising means on said first arm for locating the container along a longitudinal axis of the conveyor track when the arm is moved to the centering position.

* * * * *